United States Patent [19]

Moller et al.

[11] Patent Number: 5,710,132
[45] Date of Patent: Jan. 20, 1998

[54] USE OF BOVINE COLOSTRAL MILK AS A PREPARATION FOR THE PROTECTION OF THE LIVER

[75] Inventors: Wolfgang Moller, Oberursel; Reinhard Lissner, Gonz-Weilbach; Dietrich Nitsche, Kiel, all of Germany

[73] Assignee: Biotest Pharma GmbH, Dreieich, Germany

[21] Appl. No.: 651,406

[22] Filed: May 22, 1996

Related U.S. Application Data

[63] Continuation of Ser. No. 331,310, Oct. 28, 1994, abandoned.

[30] Foreign Application Priority Data

Nov. 4, 1993 [DE] Germany ............... 43 37 654.1

[51] Int. Cl.⁶ ............... A61K 38/00; C07K 14/00
[52] U.S. Cl. ............... 514/21; 514/838; 514/893; 514/894; 530/365; 530/366; 530/414; 530/832; 424/130.1
[58] Field of Search ............... 514/21, 838, 893, 514/894; 530/365, 366, 414, 832; 424/130.1

[56] References Cited

U.S. PATENT DOCUMENTS

| | | | |
|---|---|---|---|
| 4,377,569 | 3/1983 | Plymate | 424/130.1 |
| 5,066,491 | 11/1991 | Scott et al. | 424/130.1 |
| 5,147,548 | 9/1992 | Mies et al. | 210/639 |
| 5,258,178 | 11/1993 | Cordle et al. | 424/130.1 |
| 5,260,057 | 11/1993 | Cordle et al. | 424/130.1 |

FOREIGN PATENT DOCUMENTS

| | | |
|---|---|---|
| 0046909 | 3/1982 | European Pat. Off. . |
| 0471890 | 2/1992 | European Pat. Off. . |
| 2343316 | 3/1975 | Germany . |

OTHER PUBLICATIONS

Antibiotika—Chemotherapeutika pp. 38 and 39.

Principles & Practices of Infectious Diseases pp. 208 and 209.

*Primary Examiner*—Cecilia J. Tsang
*Assistant Examiner*—Abdel A. Mohamed
*Attorney, Agent, or Firm*—Sprung Kramer Schaefer & Briscoe

[57] ABSTRACT

The invention relates to the use of colostral milk or colostral milk preparations from the cow, or fractions containing immunoglobulin prepared therefrom, as a liver protective preparation for the prevention and treatment of liver function disturbances in liver diseases, especially for the prevention of the sequelae of these diseases, such as portal encephalopathy.

11 Claims, No Drawings

USE OF BOVINE COLOSTRAL MILK AS A PREPARATION FOR THE PROTECTION OF THE LIVER

This application is a continuation of application Ser. No. 08/331,310, filed Oct. 28, 1994, now abandoned.

The invention relates to the use of colostral milk or colostral milk preparations from the cow, or of fractions containing immunoglobulin made therefrom, as a prophylactic preparation for the prevention and treatment of liver function disorders in diseases of the liver, especially for preventing the sequelae of these diseases, such as portal encephalopathy.

The liver performs many different functions in human metabolism. One of its tasks includes the formation and secretion of bile, the conversion of monosaccharides to glycogen, glycogenolysis, gluconeogenesis from proteins, the breakdown of fatty acids, the utilization and deamination of the amino acids, the formation of plasma proteins, and the detoxification and elimination of toxic metabolites. One particularly toxic metabolite is ammonia, which forms in the bacterial breakdown of proteins in the intestine and in the breakdown of the amino acids in the liver itself. Ammonia is metabolized to urea in the healthy liver via the urea cycle, or is detoxified via glutamic acid.

In the industrialized countries at least 1 to 2% of the population suffers from chronic liver insufficiency due to a damaged liver parenchyma. In addition to acute and chronic hepatitis, fatty liver and cirrhosis of the liver, among other disorders, are considerably prominent.

The forms of hepatitis include hepatocellular diseases which are connected with an inflammatory reaction of liver tissue to viral and bacterial infections or drugs or alcohol intoxication. Some of the acute forms result in a chronic hepatitis, which in turn can lead to cirrhosis of the liver.

Cirrhosis of the liver is a chronic liver disease in which parenchymal necrosis may ensue in a repairing of the parenchyma with an increase in the connective tissue. In addition to viral hepatitis the chronic abuse of alcohol is the main cause of the occurrence of liver cirrhosis.

Various forms of liver cirrhosis are to be distinguished. In the inactive, compensated form there is only a moderate liver cell insufficiency. The active form is characterized by acute dystrophic episodes or a severe liver cell insufficiency extending even to a pre-comatose or comatose state. In the severest form, of decompensated cirrhosis, it is characterized by portal hypertension, esophageal varices, and ascites. In the terminal stage with collapse of the liver functions death occurs usually by bleeding from esophageal varices or in a coma hepaticum.

The modern methods for treatment of liver disorders, and especially the terminal stage of liver cirrhosis, have produced the result that in recent years the life expectancy of the patients has been increasing, and increasing numbers of patients with severe parenchymal damage are reaching the final stage of portal hypertension. In this narrowing of the portal vein an elevated pressure occurs in the portal vein system due to mechanical obstructions of flow in the liver. The result is then the clinical symptoms of bleeding from esophageal varices and portal encephalopathy.

While it is possible to control bleeding from esophageal varices by surgery, and portal hypertension can be relieved by the installation of shunts, the portal encephalopathy is worsened by these procedures.

In portal encephalopathy neurologic and psychopathological disorders occur due to poisoning by intoxication by ammonia and other breakdown products of proteins, manifested by depression, fatigue, loss of drive, mental disturbances, and on up to unconsciousness and hepatic coma. 30 to 40% of liver cirrhosis patients die in coma hepaticum.

Normally, in persons with an intact liver function, the ammonia developing in the gut during digestion, along with other protein breakdown products, are detoxified in the liver. If a shunt system has spontaneously formed or has been formed surgically, due to portal hypertension these toxins bypass the liver and enter directly into the circulation and thus directly into the brain. The ensuing break-down phenomena are referred to as exogenic liver failure coma.

Endogenic liver failure coma is characterized by extensive liver necrosis with loss of the natural detoxification function subsequent to viral hepatitis or poisoning.

While the ammonia level in the healthy person amounts to only about 30 to 80 µg per 100 ml of plasma, this toxin accumulates in liver cirrhosis patients to as much as 500 µg/100 ml in the plasma. It is precisely in the case of such high concentrations, which heretofore were in no way accessible to treatment, that the severest symptoms of neurological failure have been observed.

Treatment of the causes of most chronic liver disorders is not possible; instead treatment plans are limited substantially to change of diet and discontinuation of harmful substances (e.g., alcohol). So-called "liver protectants" are intended to relieve the liver of some of its other metabolic functions, so that it can regain its ability to detoxify the organism insofar as possible.

Among the liver protectant preparations are, for example, the carbohydrate lactulose, or milk containing live *Lactobacillus bifidus* bacteria, which suppress the formation of ammonia by intestinal bacteria and thus relieve the burden on the liver. Side effects of these dietetic measures are flatulence and diarrhea. Also, the high carbohydrate content of lactulose can constitute a problem.

As another dietetic approach, the attempt is made to intervene in the urea and citrate cycle by administering the ammonia-lowering amino acids ornithine and aspartate and promoting the elimination of the ammonia formed as metabolite. The amino acids aspartic acid and glutamic acid can detoxify ammonia by amidation. This therapy with amino acids, however, is promising only in the early stages of liver damage.

To reduce the formation of ammonia in cases of liver damage, the attempt is also made largely to avoid the amino acids threonine, serine, tryptophan, histidine, glutamine and glycine in the diet and to limit intake of the essential amino acids threonine and histidine to the essential level, since these amino acids are broken down to ammonia and raise the ammonia level in the plasma.

Dietetic control by amino acids and proteins is always a balancing act between the input of nitrogen with the consequent potential increase of the ammonia and the necessity of providing the patients with essential amino acids. The patients are usually directed to a high-calorie diet which should also include proteins. Liver cirrhosis patients therefore are fed as long as possible on an especially protein-rich diet, soft-curd cheese (casein from milk) being especially preferred. But since these patients' protein tolerance becomes increasingly poorer as parenchymal damage advances, this again results in a rise of the ammonia level in the plasma. For example, the intake of normal milk (0.5 g powdered milk per kilogram body weight) leads to an increase of the blood ammonia level in healthy people as well as in cirrhosis patients (Gorski, M. et al., Pol. Arch. Med. Wewn 1970, 44 (2), 115-9).

All the more surprising was the finding that, with the administration of about the same amount of protein from bovine colostral milk or from the whey from this colostral milk, the blood ammonia level in patients with liver cirrhosis can be lowered drastically. The decrease of the ammonia in some cases goes so far that even the natural level is also definitely lowered.

The term, "colostral milk," is to be understood as the milk of the first five days after calving. The colostral milk of the first three days is preferred, and that of the first day after calving is especially preferred, since here the content of the immunoglobulins is highest and the antibodies in the colostral milk are especially important for their effectiveness.

The therapeutic use of colostral milk and of protein fractions from colostral milk has until now been limited substantially to the therapy or prophylaxis of diarrheal diseases caused by bacteria, viruses or protozoa, such as E. coli, rotavirus or cryptosporidia. Examples have been described in Tacket, C. et al., The New England Journal of Medicine (1988), 318, 1240–12043; in Davidson, G. et al., The Lancet 23 Sept. 1989, 709–712, and in Rump, J. et al., Clin. Investig. (1992), 70, 588–594.

It has been shown by Prokopiv, M., Vrach Delo 4, 100–102 (1988), that in patients with multiple sclerosis, an inflammatory disease of the central nervous system, the plasma level of the liver enzymes, alanine-amino-transferase, aspartate-amino-transferase and sorbitol-dehydrogenase can be slightly reduced by the twice-daily administration of 500 ml of human colostrum over 6 weeks. In these patients there was no indication of any liver disease, but these enzymes in liver membrane entered into the plasma on account of the increased membrane permeability which is generally found in multiple sclerosis. Human colostrum, whose composition is very different from bovine colostrum, is accordingly appropriate for supportive treatment for the retardation of membrane defects in multiple sclerosis. A therapeutic action of colostral bovine milk in liver diseases, in which there is not only an increase in membrane permeability but also massive cell degeneration and disintegration, and especially an action against the toxic sequelae of protein degradation products, has never yet been described.

But surprising, and never before known, was the finding that by an oral or enteral administration of colostral milk from the cow it is possible to reduce the toxic protein metabolites such as ammonia, and that the ability of the liver to detoxify these substances can be improved.

This makes it possible to provide the patients with large amounts of protein, and thus with essential amino acids, without having to fear the harmful effects of such management, such as the massive occurrence in the blood of protein degradation products, such as ammonia.

The treatment according to the invention is performed preferably with a skimmed bovine colostral milk or with colostral whey, as it is described, for example, in Patent Applications EP 0 338 229

To achieve optimum prophylactic action, the preparations should be germ-free or at least low in bacteria. Otherwise contamination of the colostral milk with bacteria and the toxins they release might cancel the therapeutic effect. In the sterilization and disinfection of colostral milk attention must be given to the nativity of the proteins in the milk, since only the intact and native proteins can exercise the protective action on the liver. Preferably the disinfection is performed by sterile filtration, since in that case the bacteria are reliably separated without the danger of releasing toxins from the bacteria.

If desired, colostral whey can be purified by further fractionation, for example by ultrafiltration to remove proteins of low molecular weight and other components with a molecular weight below 100,000 D.

The patients are treated preferably several times a day. The colostral milk preparations are drunk in the form of a solution with a protein content of 2 g/100 ml to 20 g/100 ml, preferably 10 g/100 ml. In special cases they can be administered through a stomach or duodenal feeding tube. 100 to 600 ml of a 10% solution per day is usually sufficient as a therapeutic dose in the case of a severe cirrhosis of the liver, while lesser amounts can be given in a less severe case.

The liver diseases whose sequelae can be treated according to the invention, include inflammation of the liver, virus hepatitis, toxic liver cell damage, fibrosis of the liver, cirrhosis of the liver, liver congestion, liver dystrophy, fatty degeneration of liver cells or fatty liver. The disturbances and damage whose consequences can be treated are disturbances of the detoxification function, disturbances of the excretory function of the liver, disturbances of the conjugational function of the liver, disturbances of the synthesizing function of the liver, portal hypertension due to a liver disease, or a liver failure coma, as well as intoxication by protein degradation products or ammonia. Thus, for example, ammonia intoxication during the state following a portal shunt operation can be treated, as in the case, for example, of portocaval anastomoses.

The use of the colostral milk Preparation in accordance with the invention can also be prophylactic. Especially in virus hepatitis and incipient liver insufficiency due to liver parenchyma damage, the liver is relieved of stress and its detoxification function is improved by improvement of the conjugational and excretory functions of the liver, so that the necrotic alterations of the liver are retarded. Diagnostically, this is manifested in ways including a decided reduction of the plasma level of bilirubin and of the liver enzyme $\gamma$-glutamyl transferase (GGT), an intracellular enzyme playing an important part in the metabolism of amino acids and peptides, which passes over into the plasma upon the disintegration of liver cells. Furthermore, an increase is found in the synthesis of plasma proteins such as transferrin, for example. In this manner the final stage of portal encephalopathy can be postponed.

Liver diseases such as fibrosis, liver congestion, liver dystrophy and fatty degeneration of the liver can be treated in the same manner. By the use of the colostral milk preparation in accordance with the invention, the liver is relieved of stress.

As a rule, the retardation or prevention of the rise of the ammonia level of the blood is accompanied by an improvement or elimination, of the signs of neurological breakdown.

By the corresponding preventative treatment of patients with incipient liver damage an increase in blood ammonia can be forestalled, thereby preventing these signs of breakdown.

The use of bovine colostral milk as a liver protecting preparation is also possible in treatment before and after liver transplant operations so as to assist the detoxification function of the damaged liver before the operation and to protect the new liver after transplantation against harmful metabolites.

The following examples will serve to explain the invention.

EXAMPLE 1

A 45-year-old man suffering from liver cirrhosis with portal hypertension was hospitalized due to severe bleeding from esophageal varices. As a Consequence of the circulatory shock accompanying the bleeding, liver failure was developing in the patient. The blood ammonia level rose to 170 µg/dl. The patient showed symptoms of portal encephalopathy.

The patient was then treated through a stomach feeding tube with 15 g q.i.d. of a freeze-dried bovine colostral whey preparation. The preparation was obtained from bovine colostral milk from the first milking after calving by centrifugal defatting, casein precipitation with hydrochloric acid at pH 4.5, ultrafiltration and sterile filtration of the whey, followed by drying. The preparation was administered as a 10% solution in 0.9% sodium chloride solution. Within 24 hours the blood ammonia level dropped to 10 µg/dl and remained in the normal range (30 to 80 µg/dl) over the course of the five-day treatment.

The patient's condition improved appreciably with the colostral milk protein medication. Even after one day the patient no longer showed neurological failure symptoms and was normally responsive. The blood ammonia remained low during the treatment with the colostral milk preparation.

No side effects occurred. This was especially surprising considering the clinical experience that, in this type of patient, a lowered protein tolerance is observed, and a rise in the ammonia level.

In a control group of 21 patients with the same symptomatology, who had not received colostral milk preparation and who instead had been treated conventionally with lactulose, a constantly high ammonia level of 200 to 300 µg/dl was observed throughout the observation period.

EXAMPLE 2

A 58-year-old man with liver cirrhosis was also being treated for severe bleeding from esophageal varices. As in Example 1, he suffered hemorrhagic shock and liver failure due to the bleeding. The blood ammonia level was 270 µg/dl.

Under the daily treatment with 15 g t.i.d. of the same colostral milk preparation as in Example 1, the ammonia content of the blood dropped to 90 µg/dl and remained at this level, which is but slightly above the normal range, in the course of the four days of treatment.

EXAMPLE 3

In the case of a 50-year-old woman who had developed severe liver failure postoperatively due to cirrhosis of the liver, a greatly elevated blood ammonia level of 350 µg/ml was measured at this time.

The patient was given 15 grams of the colostral milk preparation from Example 1 three times daily for five days. Under this treatment a significant lowering of the ammonia to 120 µg/100 ml was observed within 24 hours. The clinical signs of the liver function disturbance were positively influenced under the colostral milk therapy, and the patient's mental condition, which was very poor prior to the treatment, improved rapidly with the administration of the colostral milk preparation.

EXAMPLE 4

In the case of a 48-year-old man, liver insufficiency with an already existing cirrhosis developed 3 days after a surgical intervention, with elevated ammonia levels in the plasma.

Through a stomach feeding tube the patient received 15 g q.i.d. of the colostral milk preparation from Example 1 for four days. Under the treatment a rapid and significant lowering of the ammonia from 254 µg/100 ml to 126 µg/100 ml was observed. After four days of treatment with the colostral milk preparation the blood ammonia level amounted to 108 µg/100 ml. The clinical signs of liver function disturbance were positively affected by the colostral milk therapy. After the colostral milk preparation was stopped the blood ammonia rose again within two days to 250 mg/100 ml.

This test by omission impressively shows the effectiveness of treatment with bovine colostral milk in the fact that the lowering of the blood ammonia level is connected to the time the treatment began.

EXAMPLE 5

In a 44-year-old female patient liver insufficiency developed postoperatively on the basis of an existing cirrhosis of the liver.

Prior to treatment and on the first and third day of the three-day treatment with 20 g t.i.d. of the colostral whey preparation similar to Example 1, each dissolved in 200 ml of water, the laboratory parameters were determined, and they are presented in Table 1.

TABLE 1

|  | Before therapy | After 24 h. | After 72 h. |
|---|---|---|---|
| GGT (U/l) | 105 | 97 | 78 |
| Transferrin (mg/100 ml) | 119 | 140 | 152 |

The GGT is lowered under the treatment, while the liver's synthesizing action increases, as indicated by the increase in the transferrin level.

EXAMPLE 6

A 9-year-old boy had pathologically elevated GGT levels in the plasma due to hepatitis.

After administration of 100 ml b.i.d. of a 10% colostral whey solution similar to Example 1, the levels of this liver enzyme decreased within a few days from 53 to 21 U/ml for the GGT, and remained relatively constant in this range during the treatment.

After discontinuing the medication 10 weeks later, the levels then increased again to 68 U/l.

Advantageously the colostral milk employed is one wherein per gram of protein bacteria and toxins have been reduced to less than $10^3$ germs, fat to less than 0.0 g, proteins smaller than 100,000 to less than 0.2 g and casein to less than 0.02 g.

It will be appreciated that the instant specification and the claims are set forth by way of illustration and not limitation, and that various modifications and changes may be made without departing from the spirit and scope of the present invention.

We claim:

1. A method for the improvement of liver function by reducing toxic effects on liver combined with a desirable protein-rich nutrition in patients suffering from at least one liver disorder selected from the group consisting of inflammation of the liver, virus hepatitis, toxic liver cell damage, fibrosis of the liver, cirrhosis of the liver, liver congestion, liver dystrophy, fatty degeneration of liver cells, fatty liver, disturbances of the detoxification function, disturbances of the excretory function of the liver, disturbances of the conjugational function of the liver, disturbances of the synthesizing function of the layer portal hypertension due to a liver disease, or a liver failure coma, and intoxication by protein degradation products of ammonia, which comprises administering to such patient an amount effective therefor of a bovine colostral milk.

2. The method according to claim 1, wherein colostral milk is obtained in the first 5 days after calving.

3. The method according to claim 1, wherein the colostral milk is obtained in the first 3 days after calving.

4. The method according to claim 1, wherein the colostral milk is obtained in the first 24 hours after calving.

5. The method according to claim 1, wherein bacteria and toxins have been reduced in the colostral milk to less than $10^3$ germs per g protein by filtration.

6. The method according claims 1, wherein colostral milk is obtained and processed under aseptic conditions and is then sterile-filtered.

7. The method according to claim 1, wherein the milk has a protein content of about 2 g/100 ml to 20 g/100 ml and is administered orally several times daily.

8. The method according to claim 1, wherein the milk has a protein content of about 2 g/100 ml to 20 g/100 ml and is administered through a stomach or duodenal feeding tube.

9. The method according to claim 1, wherein fat in the colostral milk has been reduced to less than 0.01 g per protein by configuration.

10. The method according to claim 9, wherein casein in the colostral milk has been reduced to less than 0.02 g per g protein by filtration and configuration.

11. The method according to claim 10, wherein proteins smaller than 100,000 Daltons have been reduced in the colostral milk to less than 0.2 g per g protein by ultrafiltration.

* * * * *